(12) United States Patent
Duran et al.

(10) Patent No.: US 7,524,445 B2
(45) Date of Patent: Apr. 28, 2009

(54) METHOD FOR MAKING EPTFE AND STRUCTURE CONTAINING SUCH EPTFE, SUCH AS A VASCULAR GRAFT

(75) Inventors: Julio Duran, Morris Plains, NJ (US); Krzysztof Sowinski, Wallington, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 468 days.

(21) Appl. No.: 11/026,657

(22) Filed: Dec. 31, 2004

(65) Prior Publication Data
US 2006/0147665 A1 Jul. 6, 2006

(51) Int. Cl.
B29C 55/26 (2006.01)

(52) U.S. Cl. .................. 264/112; 264/127; 264/288.8; 264/290.2

(58) Field of Classification Search ............... None
See application file for complete search history.

(56) References Cited

U.S. PATENT DOCUMENTS

| | | | |
|---|---|---|---|
| 3,664,915 A | 5/1972 | Gore |
| 3,953,566 A | 4/1976 | Gore |
| 3,962,153 A | 6/1976 | Gore |
| 4,096,227 A | 6/1978 | Gore |
| 4,187,390 A | 2/1980 | Gore |
| 4,304,010 A | 12/1981 | Mano |
| 4,463,329 A | 7/1984 | Suzuki |
| 4,576,608 A | 3/1986 | Homsy |
| 4,596,837 A | 6/1986 | Yamamoto et al. |
| 4,743,480 A | 5/1988 | Campbell et al. |
| 4,816,339 A | 3/1989 | Tu et al. |
| 4,849,285 A | 7/1989 | Dillon |

(Continued)

FOREIGN PATENT DOCUMENTS

EP 0 087 149 A2 2/1983

(Continued)

OTHER PUBLICATIONS

PCT Notification of Transmittal of the International Search Report and the Written Opinion of the International Searching Authority, or the Declaration for International Application No. PCT/US2005/047253, Apr. 19, 2006 (2 pages).

(Continued)

*Primary Examiner*—Mary Lynn F Theisen
(74) *Attorney, Agent, or Firm*—Hoffmann & Baron, LLP (57) ABSTRACT

A method for making a vascular graft includes providing a PTFE green tube extrudate which is un-sintered, and then initially expanding the un-sintered extrudate to produce an initial node and fibril micro-structure therein. This is followed by heating the extrudate to raise the temperature thereof for a time period of sufficient duration such that the extrudate is partially sintered. The partially sintered extrudate is subsequently expanded to make the vascular graft. The subsequent expansion produces a subsequent node and fibril micro-structure in the vascular graft. An alternative method for making a vascular graft includes providing a PTFE green tube extrudate which is un-sintered, longitudinally expanding the un-sintered extrudate to form an ePTFE tube structure, and radially expanding the un-sintered ePTFE tube structure. ePTFE made according to the method is fabricated into various structures, such as tube structures, filament structures, and sheet structures.

14 Claims, 10 Drawing Sheets

U.S. PATENT DOCUMENTS

| | | | |
|---|---|---|---|
| 4,902,423 A | 2/1990 | Bacino |
| 4,957,669 A | 9/1990 | Primm |
| 4,973,609 A | 11/1990 | Browne |
| 5,071,609 A | 12/1991 | Tu et al. |
| 5,141,522 A | 8/1992 | Landi |
| 5,192,310 A | 3/1993 | Herweck et al. |
| 5,207,960 A | 5/1993 | Moret de Rocheprise |
| 5,326,355 A | 7/1994 | Landi |
| 5,433,909 A | 7/1995 | Martakos et al. |
| 5,449,373 A | 9/1995 | Pinchasik et al. |
| 5,462,781 A | 10/1995 | Zukowski |
| 5,620,763 A | 4/1997 | House et al. |
| 5,628,786 A | 5/1997 | Banas et al. |
| 5,641,373 A | 6/1997 | Shannon et al. |
| 5,716,660 A | 2/1998 | Weadock et al. |
| 5,718,973 A | 2/1998 | Lewis et al. |
| 5,733,303 A | 3/1998 | Israel et al. |
| 5,735,892 A | 4/1998 | Myers et al. |
| 5,749,880 A | 5/1998 | Banas et al. |
| 5,800,512 A | 9/1998 | Lentz et al. |
| 5,810,870 A | 9/1998 | Myers et al. |
| 5,814,405 A | 9/1998 | Branca et al. |
| 5,840,775 A | 11/1998 | Howard, Jr. et al. |
| 5,843,173 A | 12/1998 | Shannon et al. |
| 5,858,556 A | 1/1999 | Eckert et al. |
| 5,861,033 A | 1/1999 | Martakos et al. |
| 5,897,587 A | 4/1999 | Martakos et al. |
| 5,925,075 A | 7/1999 | Myers et al. |
| 5,928,279 A | 7/1999 | Shannon et al. |
| 5,972,018 A | 10/1999 | Israel et al. |
| 5,976,192 A | 11/1999 | McIntyre et al. |
| 5,980,799 A | 11/1999 | Martakos et al. |
| 6,001,125 A | 12/1999 | Golds et al. |
| 6,004,348 A | 12/1999 | Banas et al. |
| 6,010,529 A | 1/2000 | Herweck et al. |
| 6,048,484 A | 4/2000 | House et al. |
| 6,053,943 A | 4/2000 | Edwin et al. |
| 6,080,198 A | 6/2000 | Lentz et al. |
| 6,124,523 A | 9/2000 | Banas et al. |
| 6,132,457 A | 10/2000 | Chobotov |
| 6,187,054 B1 | 2/2001 | Colone et al. |
| 6,203,735 B1 | 3/2001 | Edwin et al. |
| 6,214,039 B1 | 4/2001 | Banas et al. |
| 6,264,684 B1 | 7/2001 | Banas et al. |
| 6,267,834 B1 | 7/2001 | Shannon et al. |
| 6,306,162 B1 | 10/2001 | Patel |
| 6,319,279 B1 | 11/2001 | Shannon et al. |
| 6,383,214 B1 | 5/2002 | Banas et al. |
| 6,395,208 B1 * | 5/2002 | Herweck et al. ............ 264/127 |
| 6,402,779 B1 | 6/2002 | Colone et al. |
| 6,416,537 B1 | 7/2002 | Martakos et al. |
| 6,428,571 B1 | 8/2002 | Lentz et al. |
| 6,443,981 B1 | 9/2002 | Colone et al. |
| 6,451,047 B2 | 9/2002 | McCrea et al. |
| 6,488,701 B1 | 12/2002 | Nolting et al. |
| 6,605,119 B1 | 8/2003 | Colone et al. |
| 6,616,876 B1 * | 9/2003 | Labrecque et al. .......... 264/119 |
| 6,699,276 B2 | 3/2004 | Sogard et al. |
| 6,719,783 B2 | 4/2004 | Lentz et al. |
| 6,758,858 B2 | 7/2004 | McCrea et al. |
| 6,786,920 B2 | 9/2004 | Shannon et al. |
| 6,790,225 B1 | 9/2004 | Shannon et al. |
| 6,797,217 B2 | 9/2004 | McCrea et al. |
| 2001/0050132 A1 | 12/2001 | Shannon et al. |
| 2002/0111667 A1 | 8/2002 | Girton et al. |
| 2002/0198588 A1 | 12/2002 | Armstrong et al. |
| 2003/0028240 A1 | 2/2003 | Nolting et al. |
| 2003/0135266 A1 | 7/2003 | Chew et al. |
| 2004/0024442 A1 | 2/2004 | Sowinski et al. |
| 2004/0193242 A1 | 9/2004 | Lentz et al. |
| 2007/0276471 A1 * | 11/2007 | Duran ....................... 623/1.39 |

FOREIGN PATENT DOCUMENTS

| | | |
|---|---|---|
| EP | 0 437 721 A1 | 12/1990 |
| EP | 0 707 033 A1 | 4/1995 |
| GB | 1506432 | 4/1978 |
| WO | WO 96/00103 | 1/1996 |

OTHER PUBLICATIONS

PCT International Search Report for International Applicaiton No. PCT/US2005/047253, Apr. 19, 2006 (6 pages).

PCT Written Opinion for International Application No. PCT/US2005/047253, Apr. 19, 2006 (7 pages).

Odian, "Principles of Polymerization, Second Edition", A Wiley-Interscience Publication, John Wiley & Sons, Inc., New York, et al., 1981, pp. 25 to 33.

* cited by examiner

Ways of achieving Partially Sintered PTFE Material
    (1) low temperature, long time
    (2) high temperature, short time
    (3) temperature below (sinter temperature), short time

METHOD FOR MAKING EPTFE AND STRUCTURE CONTAINING SUCH EPTFE, SUCH AS A VASCULAR GRAFT

FIELD OF THE INVENTION

The present invention relates generally to a method for making structures including expanded polytetrafluoroethylene (PTFE). More specifically, the present invention relates to such a method in which a PTFE structure is expanded, partially sintered and further expanded. The present invention further relates to a structure containing ePTFE made according to the method, such as an ePTFE tube structure for a vascular graft.

BACKGROUND OF THE INVENTION

It is well known to use extruded tube structures of polytetrafluoroethylene (PTFE) as implantable intraluminal prostheses, particularly vascular grafts. PTFE is particularly suitable as an implantable prosthesis as it exhibits superior biocompatibility. PTFE tube structures may be used as vascular grafts in the replacement or repair of a blood vessel as PTFE exhibits low thrombogenicity. In vascular applications, the grafts are manufactured from expanded polytetrafluoroethylene (ePTFE) tube structures. These tube structures have a microporous micro-structure which allows natural tissue ingrowth and cell endothelization once implanted in the vascular system. This contributes to long term healing and patency of the graft. Grafts formed of ePTFE have a fibrous state which is defined by the interspaced nodes interconnected by elongated fibrils.

It is known to form an ePTFE tube structure from an extruded PTFE green tube structure. Such a green tube structure can be longitudinally expanded into an ePTFE tube structure which has a substantially larger longitudinal dimension in relation to the initial longitudinal dimension of the green tube structure. Such longitudinal expansion creates a node and fibril micro-structure which may be locked by sintering the ePTFE tube structure. The sintered ePTFE tube structure may then be further expanded to further change the dimensions or other characteristics or properties of the ePTFE tube structure. For example, the sintered ePTFE tube structure may be radially expanded to increase the diameter thereof.

One disadvantage of known methods of expanding an extruded PTFE green tube structure is that such methods typically provide for the green tube structure to initially be longitudinally expanded and then fully sintered. Further expansion of such a fully sintered ePTFE tube structure, such as by radial expansion thereof, may be difficult. For example, radial expansion of a fully sintered ePTFE tube structure typically requires very careful application of radial forces to the tube structure to prevent damage thereto during such expansion. More specifically, very precise force magnitudes and application rates thereof may be required, for example, to prevent tearing of the tube structure. Such precise control of the force application and possibly other conditions makes such further expansion difficult. The difficulty of such further radial expansion increases as the magnitude of such expansion increases. If further expansion of a fully sintered ePTFE tube structure is not properly performed, then significant portions of the sintered ePTFE tube structures may be damaged by such further expansion.

Thus, there is a need for a method for making PTFE tube structures for vascular grafts to facilitate further expansion of longitudinally expanded ePTFE tube structures.

SUMMARY OF THE INVENTION

The method for making an ePTFE structure of the present invention includes providing an extruded PTFE structure, referred to herein as PTFE extrudate, which is un-sintered, and then initially expanding the un-sintered PTFE extrudate to produce an initial node and fibril micro-structure therein. This is followed by heating the initially expanded ePTFE structure to raise the temperature thereof for a time period of sufficient duration such that the ePTFE structure is partially sintered. The partially sintered ePTFE structure constitutes an intermediate which is subsequently expanded. The subsequent expansion produces a subsequent node and fibril micro-structure in the ePTFE structure. The method may be used to make ePTFE tube structures from PTFE green tube extrudate. Also, the method may be used for making other ePTFE structures, such as a cover for a stent which may be implanted in the body of a patient. Additionally, the method may be used for making a sheet, plate and rod of ePTFE material. Moreover, the method may be used for making an ePTFE monofilament which may be incorporated into a fabric material, such as by weaving, knitting or braiding. Each of these sheets, plates and fabric materials may be implanted in or on the body of a patient.

The partial sintering of the ePTFE structure which has been initially expanded facilitates the subsequent expansion thereof. For example, partial sintering of a longitudinally expanded ePTFE tube structure facilitates subsequent radial expansion thereof. This results from the node and fibril micro-structure produced from the initial longitudinal expansion and the partial sintering being deformable and having an increased resistance to tears and the like during such deformation. This provides higher useful product yields from such subsequent radial expansion.

The partial sintering of an ePTFE tube structure which has been previously expanded is particularly advantageous for subsequent expansions thereof which are substantial in amount. In contrast, if an expanded ePTFE tube structure is fully sintered and then subsequently expanded, then considerable amounts of tears and the like in the tube structure can be expected. Accordingly, partial sintering of an ePTFE tube structure which has been longitudinally expanded facilitates subsequent radial expansion thereof where such radial expansion is desired to substantially increase the radial dimension of the tube structure. Also, radial expansion of a longitudinally expanded ePTFE tube structure which has been partially sintered is facilitated where such radial expansion is desired to produce a tapered portion of the tube structure between portions thereof which have different radial dimensions. Additionally, a component of a bifurcated ePTFE tube structure, such as an ePTFE tube structure which constitutes the trunk or one or more branches thereof, may be longitudinally expanded and subsequently radially expanded before the component is assembled to the bifurcated ePTFE tube structure. Such subsequent radial expansion is facilitated when the component is partially sintered after the longitudinal expansion and before the radial expansion thereof.

An alternative embodiment of the method of the present invention includes providing a PTFE green tube extrudate which is un-sintered, longitudinally expanding the un-sintered extrudate, and radially expanding the un-sintered, longitudinally expanded, extrudate. Radial expansion of the longitudinally expanded, un-sintered tube structure, as compared to a partially or fully sintered ePTFE tube structure, also results in higher yields because the longitudinally expanded, un-sintered tube structure is deformable and has an increased resistance to tears and the like during such deformation.

ePTFE which is made according to the method of the present invention may be fabricated into various structures, such as the aforementioned tube structures. Additionally, the ePTFE may be fabricated into filament structures which may be incorporated into a fabric material. Also, the ePTFE may be fabricated into a sheet structure. Further, both the fabric material and sheet structure may be formed into respective tube structures.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
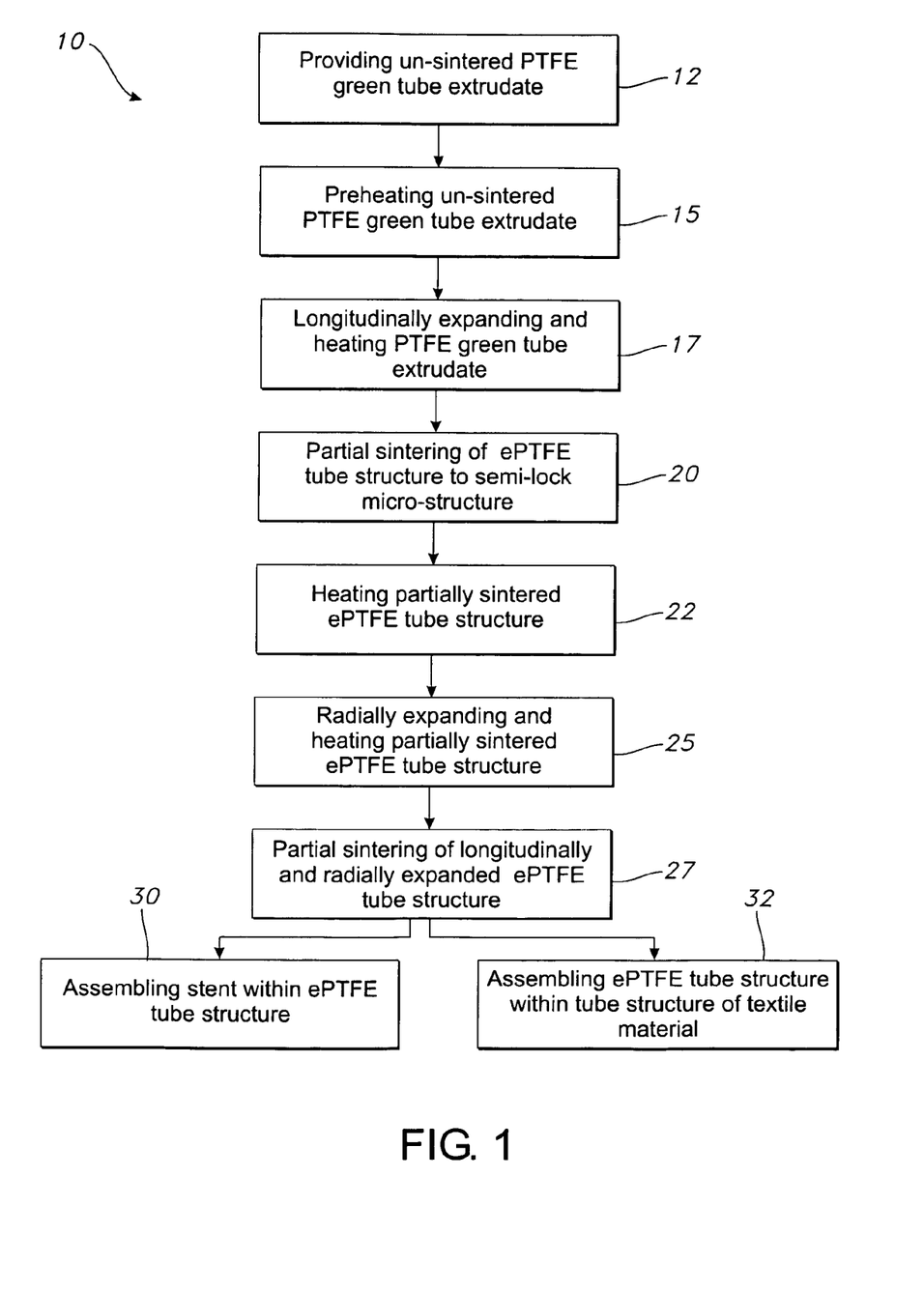
FIG. 1 is a block diagram showing a method for making a vascular graft of the present invention, the method including initially expanding an un-sintered extrudate, partially sintering the extrudate, and subsequently expanding the extrudate.

Referring to the drawings and more particularly to FIG. 1, a method 10 for making an ePTFE structure is shown in the block diagram thereof. The ePTFE structure which is made according to the method 10 is a vascular graft. Alternative embodiments of the method 10 may be used to make other ePTFE structures, such as a cover for a stent, sheet, plate, rod and mono-filament. The method 10 for making a vascular graft includes providing PTFE green tube extrudate which is un-sintered 12, and pre-heating the extrudate 15. The pre-heating 15 may be, for example, at a temperature of from approximately room temperature to 500 degrees F.

The pre-heated un-sintered PTFE green tube extrudate is longitudinally expanded with continued heating thereof 17. The continued heating may be at temperatures of up to approximately 600 degrees F., such as 500 degrees F. An expanded PTFE green tube extrudate is referred to herein as an ePTFE tube structure. The longitudinal expansion 17 may increase the longitudinal dimension of the extrudate by between approximately 10% and 10,000%. In a preferred embodiment, the longitudinal dimension may be increased by between approximately 200% and 6,000%. The rate of such expansion may be between approximately 1 and 100 cm/sec., such as 35 cm/sec. The longitudinal expansion with continued heating 17 produces an initial node and fibril microstructure in the tube structure which is characterized by a longitudinal orientation of the ePTFE fibers and a radial orientation of the nodes, an example of which is shown in FIG. 2.

Figure 2:
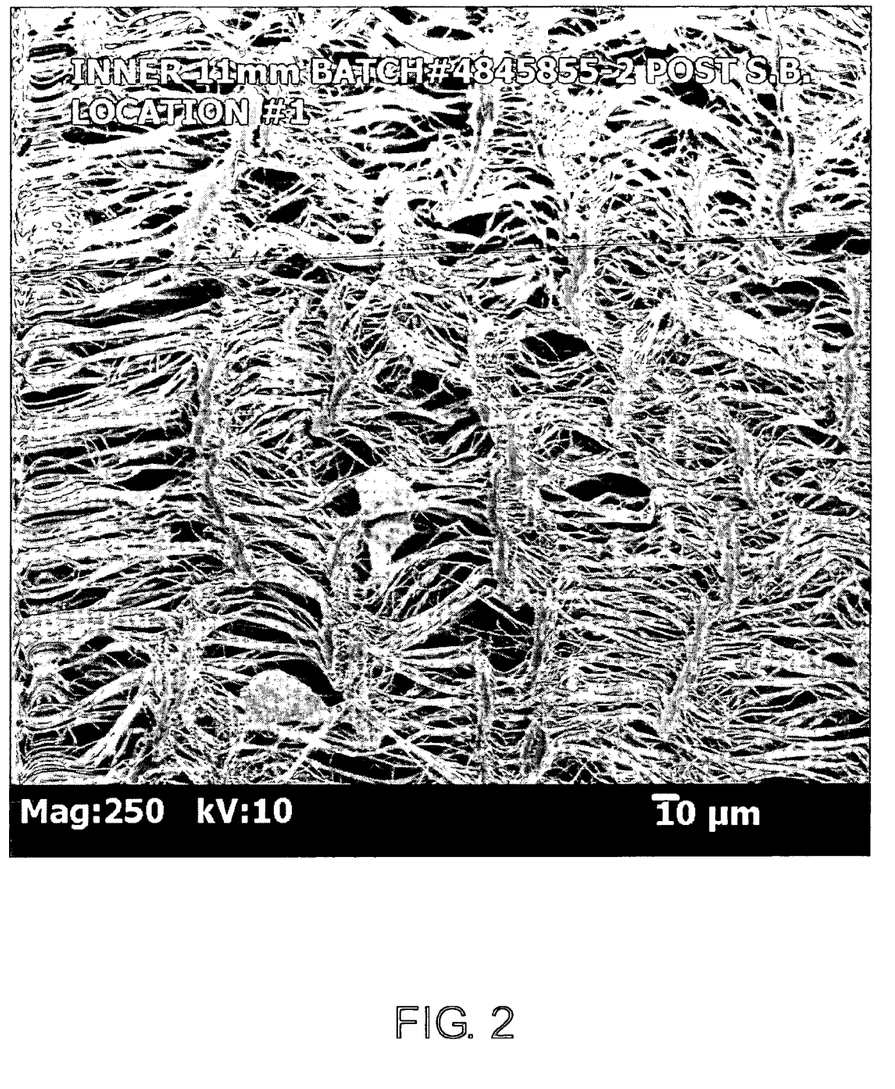
FIG. 2 is a photo-micrograph of an ePTFE tube which has been longitudinally expanded.

FIG. 2 is a photo-micrograph of the inner surface of an ePTFE tube structure which has been pre-heated, concurrently longitudinally expanded and heated, and subsequently fully sintered. Before the longitudinal expansion, the inner diameter of the PTFE tube structure was slightly greater than 11 mm. The inner diameter of the PTFE tube structure was reduced by the longitudinal expansion. The microstructure of the ePTFE tube structure was locked by the full sintering, but was otherwise not substantially affected as a result thereof. Accordingly, the photo-micrograph of FIG. 2 illustrates the microstructure of an ePTFE tube structure after the longitudinal expansion and heating thereof 17.

The longitudinally expanded ePTFE tube structure is partially sintered 20 by heating thereof to raise the temperature of the tube structure for a time period of sufficient duration such that at least a portion of the initial longitudinal expansion 17 is retained or "locked" in the structure. The partial sintering further provides for limiting the temperature and time duration such that the portion of the ePTFE tube structure in which at least a portion of the initial longitudinal expansion 17 is retained is not fully sintered. In a preferred embodiment, the PTFE tube structure remains in the same oven during both the initial longitudinal expansion 17 and partial sintering 20.

Figure 3:
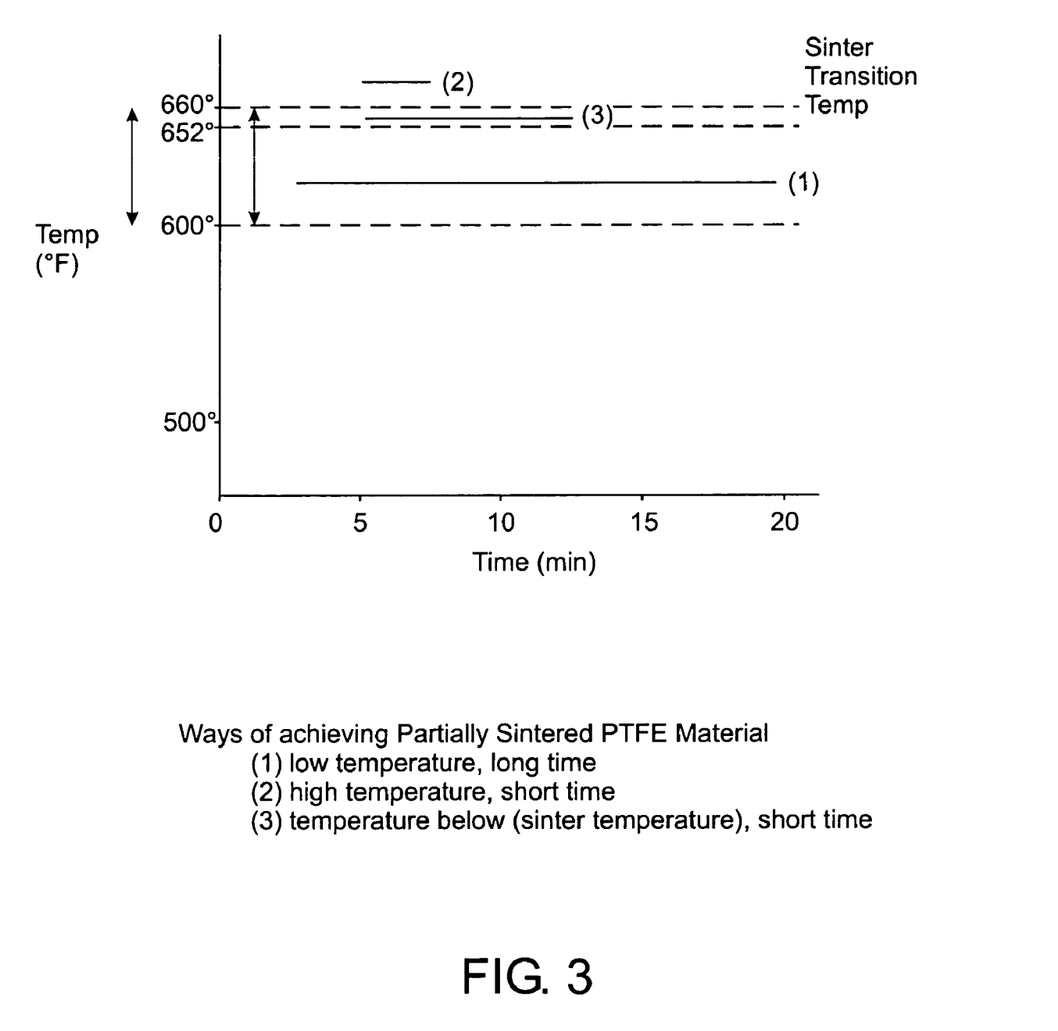
FIG. 3 is a graph showing temperatures and corresponding time durations for partial sintering of PTFE.

Examples of the temperatures and corresponding time durations which may provide the partial sintering 20 are shown in FIG. 3. The range of temperatures for the partial sintering 20 is from approximately 600 degrees F., or possibly lower, to 700 degrees F. The range of time durations for the partial sintering 20 is from approximately 1 minute to 1 hour. FIG. 3 shows that the partial sintering 20 may be provided by subjecting the ePTFE tube structure to a relatively low temperature for a relatively long time duration, or a relatively high temperature for a relatively short time duration. FIG. 3 also shows that the partial sintering 20 may occur at a temperature which exceeds the temperature at which full sintering occurs, provided the time duration of such temperature is sufficiently short. Full sintering occurs at temperatures between approximately 652 degrees F. and 660 degrees F. It is possible for the entire ePTFE tube structure to be partially sintered 20, or alternatively, the partial sintering may be applied to selected portions of the structure, such as longitudinal sections.

Figure 4:
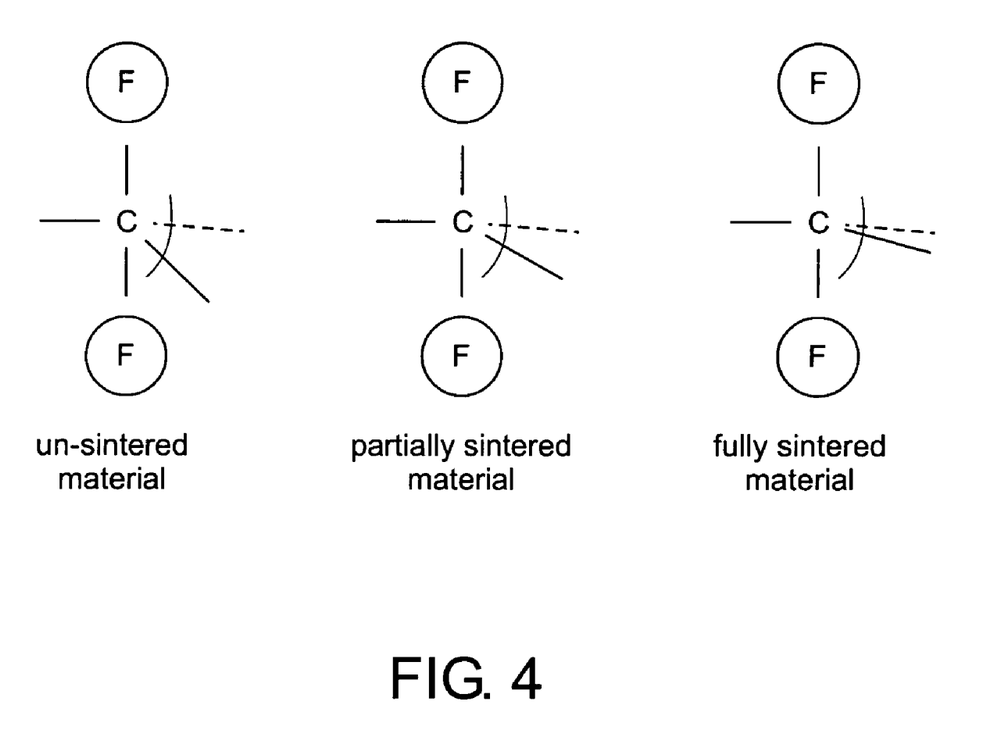
FIG. 4 is a schematic view of the range of rotation of carbon atoms in un-sintered PTFE, partially sintered PTFE, and fully sintered PTFE.

The partial sintering 20 produces a semi-locked micro-structure of the ePTFE tube structure. FIG. 4 shows a schematic view of the range of motion of carbon atoms provided by the molecular bonds therebetween in un-sintered, partially sintered, and fully sintered PTFE material. Without wishing to be bound by any one theory, it is believed that the partial sintering provides for less molecular rotation range of the adjacent atoms as compared to unsintered PTFE material, but more molecular rotational range as compared to fully sintered PTFE material. The range of motion illustrated in FIG. 4 refers to three-dimensional relative displacement between adjacent carbon atoms.

The term "partial sintering" means that the ePTFE material has been subjected to conditions of time and temperature which are insufficient to cause a fully sintered material. A "fully sintered" material means that the ePTFE material has been subjected to conditions of time and temperature such that when cooled, the polymer "fully" crystallizes or returns to a fully crystalline state. This full crystallization is to be considered "100%" crystallized or the maximum amount of crystallization achievable for the material. Full crystallization is the baseline for comparison of crystallization formed from partially sintered ePTFE material.

In order to fully sinter the ePTFE material, conditions of sufficient time and temperature must be permitted to act thereon to allow sufficient molecular orientation of the polymer such that when it is permitted to cool, a highly crystalline, i.e., fully crystallized, material results. The highly crystalline form fully "locks-in" the micro-structure and requires a high degree of mechanical or thermal energy to overcome this physical form. In contrast, the partially sintered material is only partially crystallized, and thus, has a lesser degree of "locked-in" structure, i.e., a partially locked-in structure which corresponds to the degree of crystallinity.

In the fully crystallized form, there is less ability for relative molecular movement due to the crystalline structure. Less crystalline structure permits a higher degree of relative movement at the molecular level.

The degree of crystallinity reached upon subjecting the ePTFE material to appropriate conditions of time and temperature, can be measured by a variety of methods including x-ray diffraction and differential scanning calorimetry (DSC). DSC measures the heat energy absorption or heat capacity of a material as a function of temperature. An absorption peak is measured which correlates with the amount of heat energy required to undergo a thermal transition and change from the crystalline form to the melt form of the polymer. A fully sintered material, which has a maximum crystallization structure, provides a base-line for determining the degree of crystallinity achieved through partial sintering. Since the parameters of time and temperature for partial sintering will generally be less than those required for full sintering, there is less opportunity for full molecular orientation of the polymer and concomitantly less crystalline morphology once the polymer is cooled. An ePTFE structure which is partially sintered may have a micro-structure for which the degree of crystalline structure is about 10% to 90% of a fully sintered and fully recrystallized micro-structure.

Thus, an ePTFE structure which is partially sintered in accordance with the present invention, can be subjected to further expansion with less likelihood of tearing of the ePTFE material, since less of the crystalline structure is present, thereby requiring less force or energy to produce the further expansion then would otherwise be required if the ePTFE structure was fully sintered and fully crystallized.

Following the partial sintering 20, the ePTFE tube structure is again heated 22. Subsequent to the heating 22, the ePTFE tube structure is radially expanded with continued heating thereof 25 to increase the diameter thereof. The radial expansion 25 may increase the radial dimension of the ePTFE tube structure by between approximately 10% and 600%. Also, the radial expansion 25 may result in the inner diameter of an ePTFE tube structure increasing from approximately 11 mm to 36 mm. The radial expansion of the ePTFE tube structure 25 produces a subsequent node and fibril micro-structure therein, an example of which is shown in FIG. 5.

Figure 5:
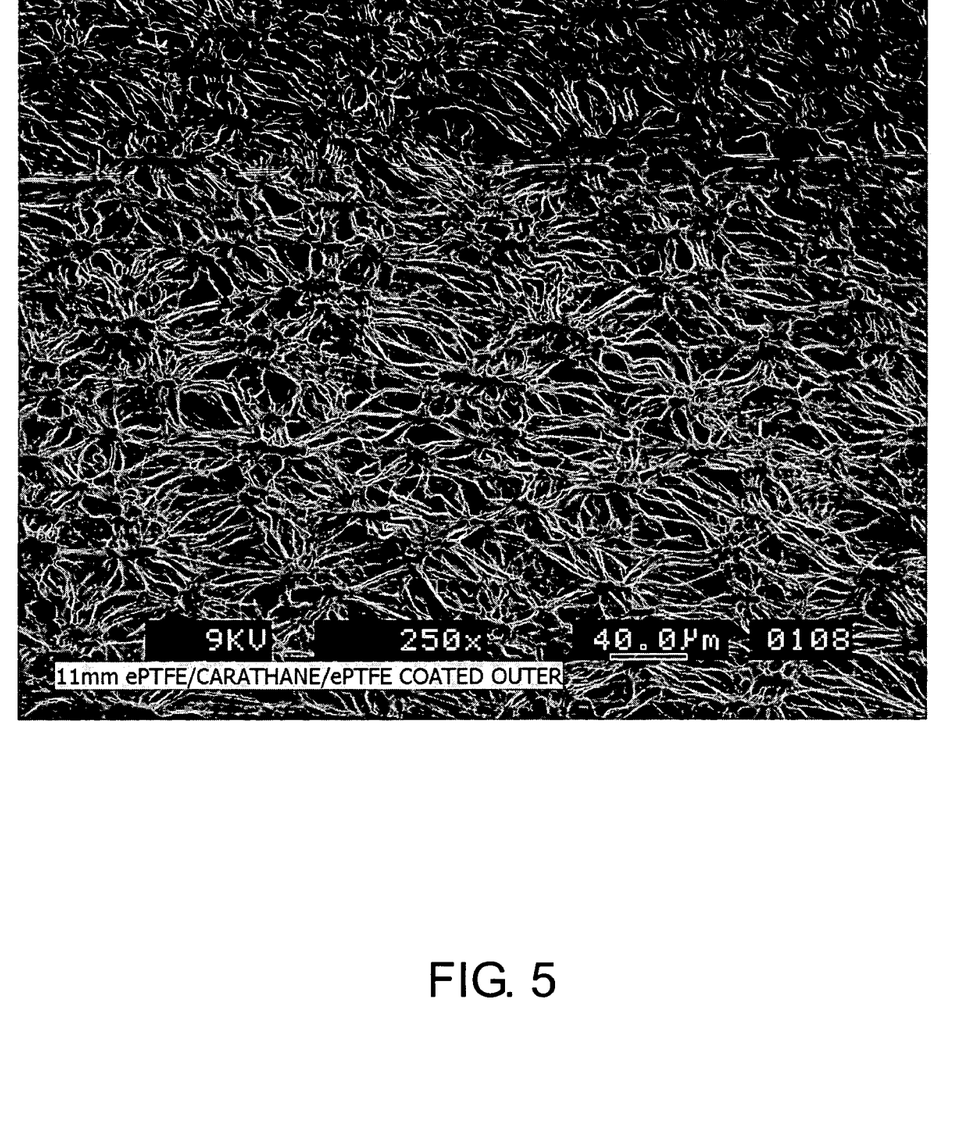
FIG. 5 is a photo-micrograph of an ePTFE tube which has been longitudinally expanded, partially sintered and radially expanded.

FIG. 5 is a photo-micrograph of the outer surface of an ePTFE tube structure which has been longitudinally expanded, such as by step 17 in FIG. 1, partially sintered, such as by step 20 in FIG. 1, and radially expanded, such as by step 25 in FIG. 1. Before the radial expansion, the inner diameter of the PTFE tube structure was approximately 11 mm. The inner diameter of the PTFE tube structure was increased by the radial expansion to approximately 36 mm. Following the radial expansion 25, the ePTFE tube structure is partially sintered 27 to partially lock the micro-structure thereof. Alternatively, it is possible for the ePTFE tube structure to be fully sintered to completely lock the micro-structure thereof following the radial expansion 25.

Following the partial sintering 27 or possibly after the full sintering thereafter, the ePTFE tube structure may have a stent assembled thereto such that the stent is within the tube structure 30. The assembly 30 may include the insertion of the stent within the ePTFE tube structure.

Alternatively, the partial sintering 27 or possibly the full sintering thereafter, may be followed by arranging the ePTFE tube structure within a tube structure formed of textile material. In a preferred embodiment, the tube structures are in coaxial relation to one another and are bonded together. An alternative arrangement is possible in which the tube structure formed of textile material is within the ePTFE tube structure such that the tube structures are in coaxial relation to one another and bonded together.

Alternatives to the steps of the method 10 illustrated in FIG. 1 are possible within the scope of the invention. For example, it is possible for the partial sintering 20 to be preceded by a radial expansion of the PTFE green tube extrudate and followed by a longitudinal expansion thereof. Radial expansion of an unexpanded PTFE green tube extrudate would produce an initial node and fibril micro-structure therein characterized by a radial orientation of ePTFE fibers and longitudinal orientation of the nodes. Also, the partial sintering 20 may be preceded and followed by additional expansion or other processing steps.

Figure 6:
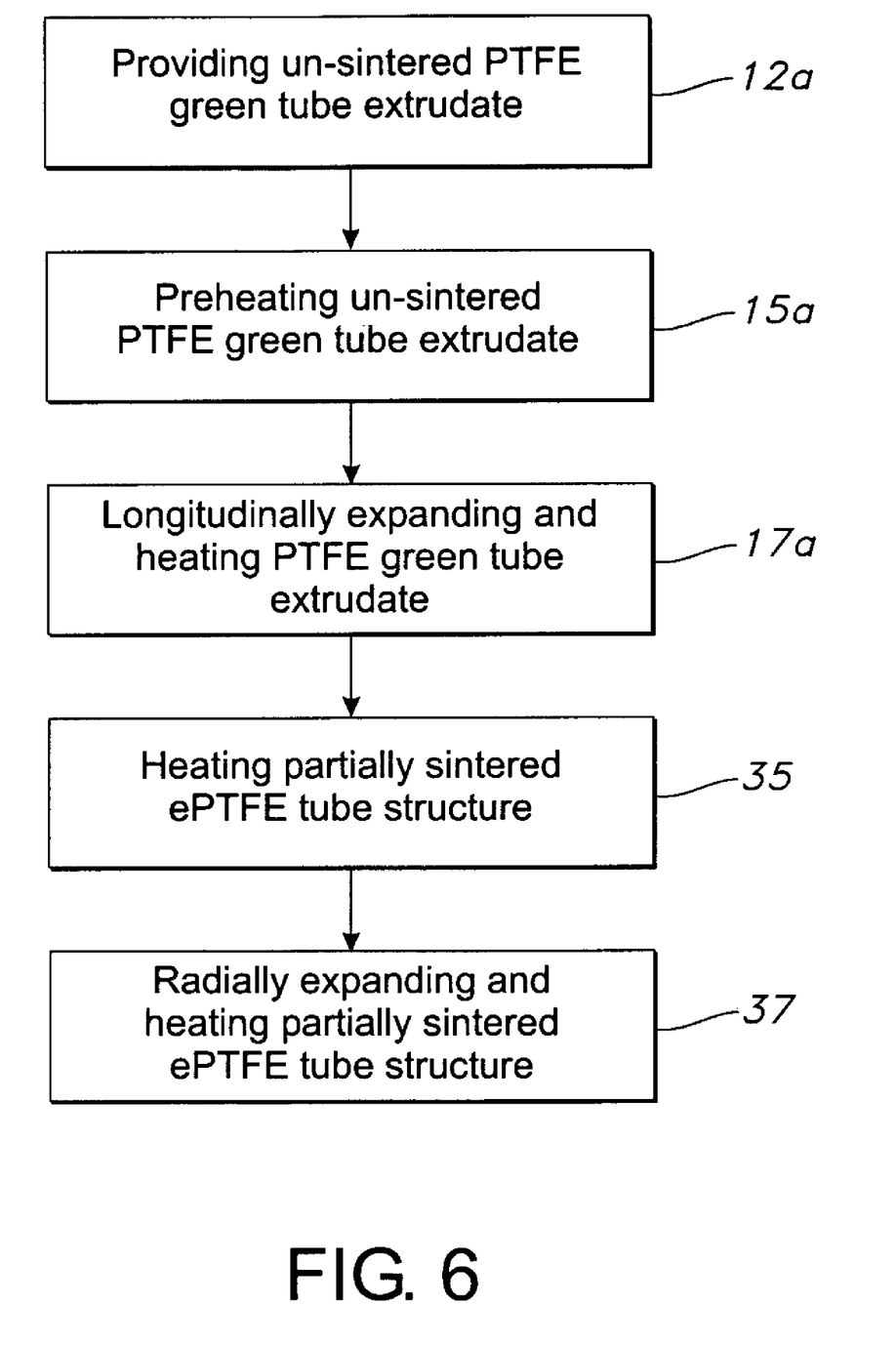
FIG. 6 is a block diagram showing an alternative embodiment of the method of FIG. 1, the alternative embodiment including longitudinal expansion followed by radial expansion of an un-sintered PTFE green tube extrudate.

An alternative embodiment for the method 10a is shown in FIG. 6. Steps illustrated in FIG. 6 which correspond to steps in FIG. 1 have, in FIG. 6, the same reference numeral as in FIG. 1 with the addition of the suffix "a". As shown in FIG. 6, the longitudinal expansion and heating 17a is followed by continued heating of the un-sintered ePTFE tube structure 35 and radial expansion and heating thereof 37. In a preferred embodiment, the tube structure is contained in a first oven during the longitudinal expansion and heating thereof 17a, and subsequently transferred to a second oven for the radial expansion and heating 37 of the tube structure. It is also possible for the radial expansion of the tube structure to be performed outside of an oven. In an alternative embodiment, it is possible for radial expansion and heating, similar to step 37 in FIG. 6, to precede the longitudinal expansion and heating, similar to step 17a in FIG. 6. Accordingly, the method 10a provides for longitudinal and radial expansion of the un-sintered PTFE green tube extrudate.

Figure 7:
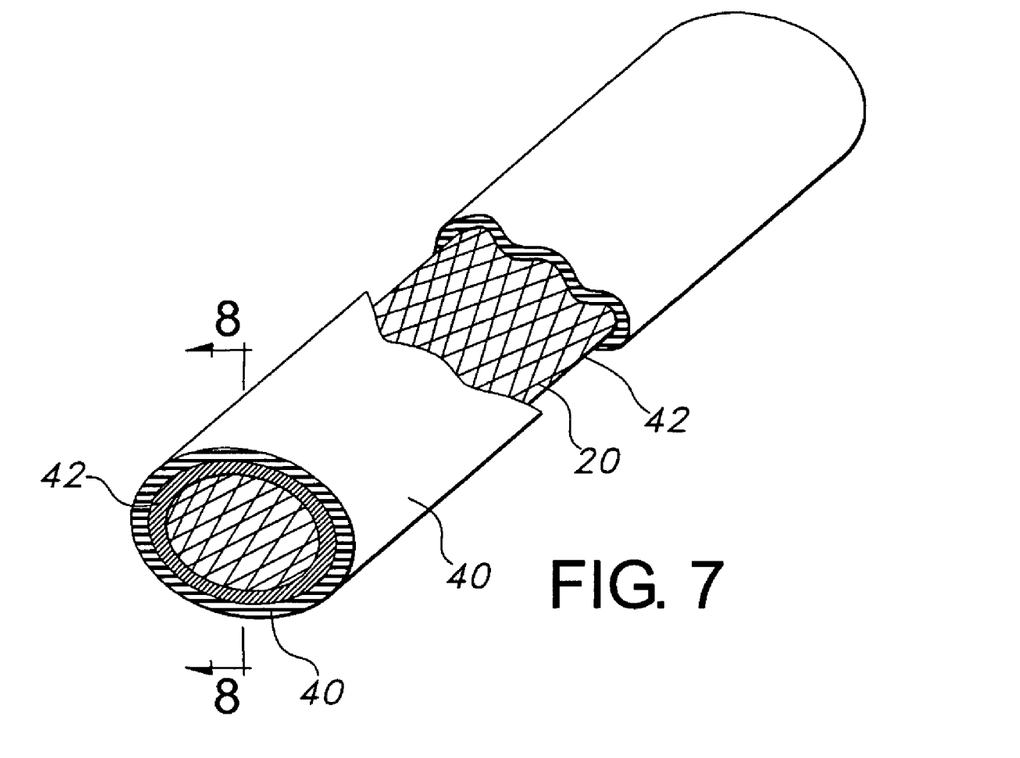
FIG. 7 is a perspective view of a vascular graft of the present invention, the vascular graft including an ePTFE tube structure and a stent therein, the ePTFE tube structure being made according to a method of the present invention.
Figure 8:
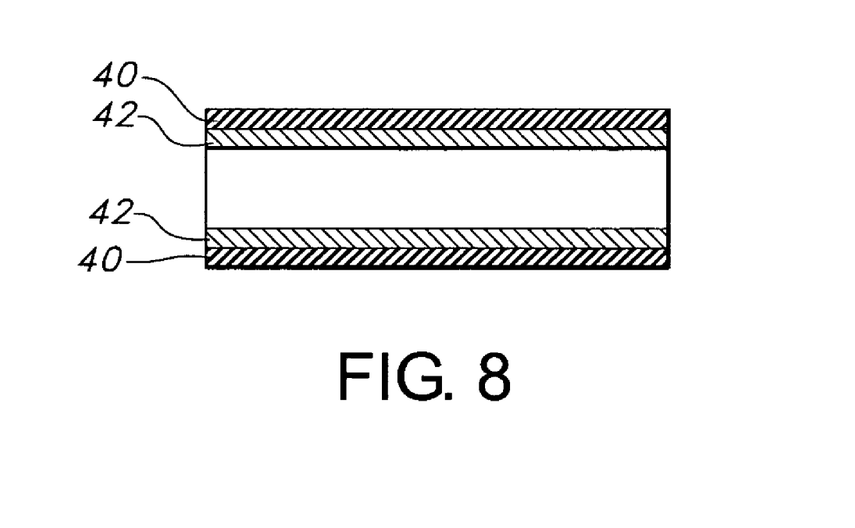
FIG. 8 is a cross-sectional view in the plane indicated by line 8-8 of FIG. 7 showing the ePTFE tube structure and stent.

The methods 10, 10a provide for the manufacture of several embodiments of a vascular graft. For example, a vascular graft including an integral ePTFE tube structure 40, such as is shown in FIG. 7, may be made according to the methods 10, 10a. The ePTFE tube structure 40 may be used in combination with a stent 42. The stent 42 is secured within the tube structure 40, as shown in FIGS. 7 and 8.

Figure 9:
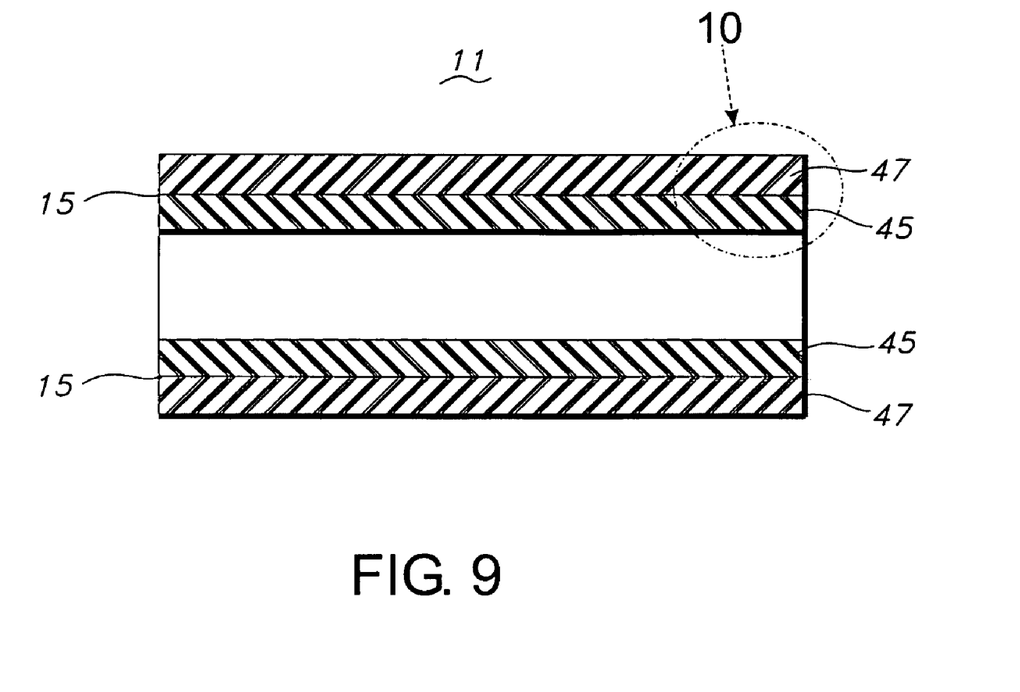
FIG. 9 is a longitudinal cross-sectional view of a vascular graft of the present invention, the vascular graft including an ePTFE tube structure within a tube formed of textile material, one or both of the tube structures being made according to a method of the present invention.
Figure 10:
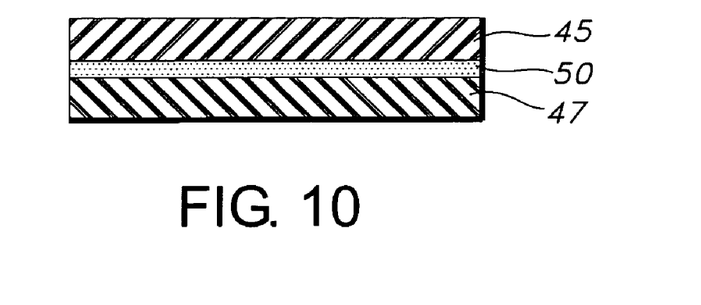
FIG. 10 is an enlarged view of the portion contained in the enclosure 10 of FIG. 9 showing the bonding material between the tube structures.

In an alternative embodiment, an ePTFE tube structure 45 may be assembled to a second tube structure 47 formed of textile material in coaxial relation therewith. The ePTFE tube structure 45 may be within the second tube structure 47, as shown in FIG. 9. The ePTFE tube structure 45 may be un-sintered, partially sintered, or fully sintered before assembly thereof to the second tube structure 47. The ePTFE tube structure 45 and second tube structure 47 are bonded together, typically by the outer surface of the ePTFE tube structure, being bonded to the inner surface of the second tube structure by an adhesive material 50, as shown in FIG. 10.

In a preferred embodiment, the adhesive material is Corethane ™ adhesive. Corethane ™ adhesive includes polycarbonate urethanes provided as an adhesive solution. The adhesive material 50 may include a sealant material. The adhesive material 50 may be applied to the tube structures 45, 47 by spraying. For example, a bonding material or sealant may be sprayed on the outer surface of the ePTFE tube structure 45 after the longitudinal and radial expansion thereof. In a further alternative embodiment, the second tube structure 47 may be within the ePTFE tube structure 45 in coaxial relation thereto and the tube structures bonded together.

Embodiments of tube structures bonded together in coaxial relation to one another which are related to the assembly of the ePTFE tube structure 45 and the second tube structure 47 are disclosed in U.S. Patent Application Publication No. US2003/0204241, the entire disclosure of which is hereby incorporated by reference herein.

Figure 11:
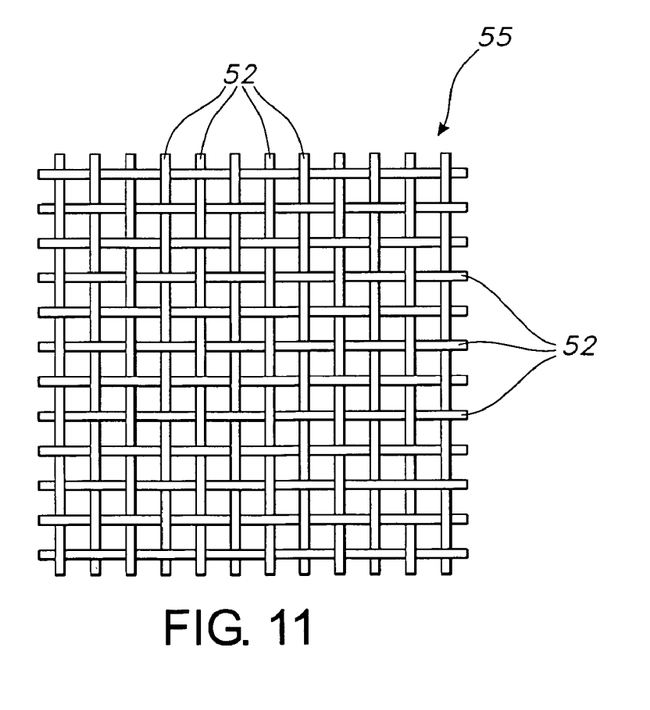
FIG. 11 is a perspective view of a fabric material of the present invention, the fabric material incorporating one or more ePTFE filament structures made according to a method of the present invention.
Figure 12:
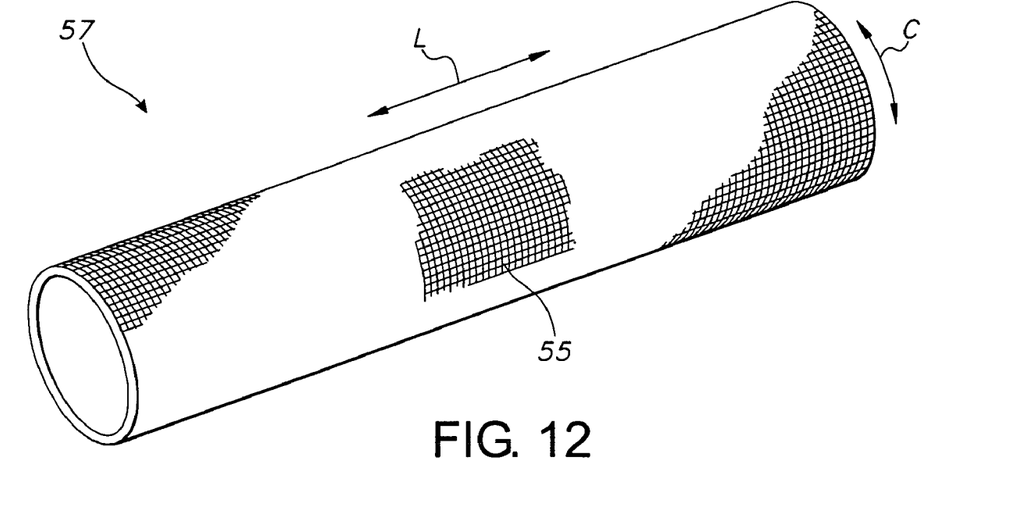
FIG. 12 is a perspective view of a vascular graft of the present invention, the vascular graft including an ePTFE tube structure formed from the fabric material of FIG. 11.

The methods 10, 10a provide for the manufacture of one or more ePTFE filaments 52 which may be incorporated into a fabric material 55, as shown in FIG. 11, such as by knitting, weaving or braiding. A portion of or all of the filaments 52 of the fabric material 55 may be made according to the methods 10, 10a. The fabric material 55 may be rolled into a cylindrical structure such that the edges thereof abut one another in an orientation which may be longitudinal or helical relative to the longitudinal axis of the cylindrical structure. The edges are bonded together such that the fabric material 55 forms a tube structure 57, as shown in FIG. 12. The tube structure 57 may be used individually, or in combination with a stent 42 as a cover therefor, such as is shown in FIGS. 7 and 8. Alternatively, the tube structure 57 may be used as either one of the tube structures 45, 47 shown in FIGS. 9 and 10. Additionally, the fabric material 55 may be shaped to have non-cylindrical contours, such as a planar or slightly curved, for use as an implant on the surface of or within the body of a patient.

Figure 13:
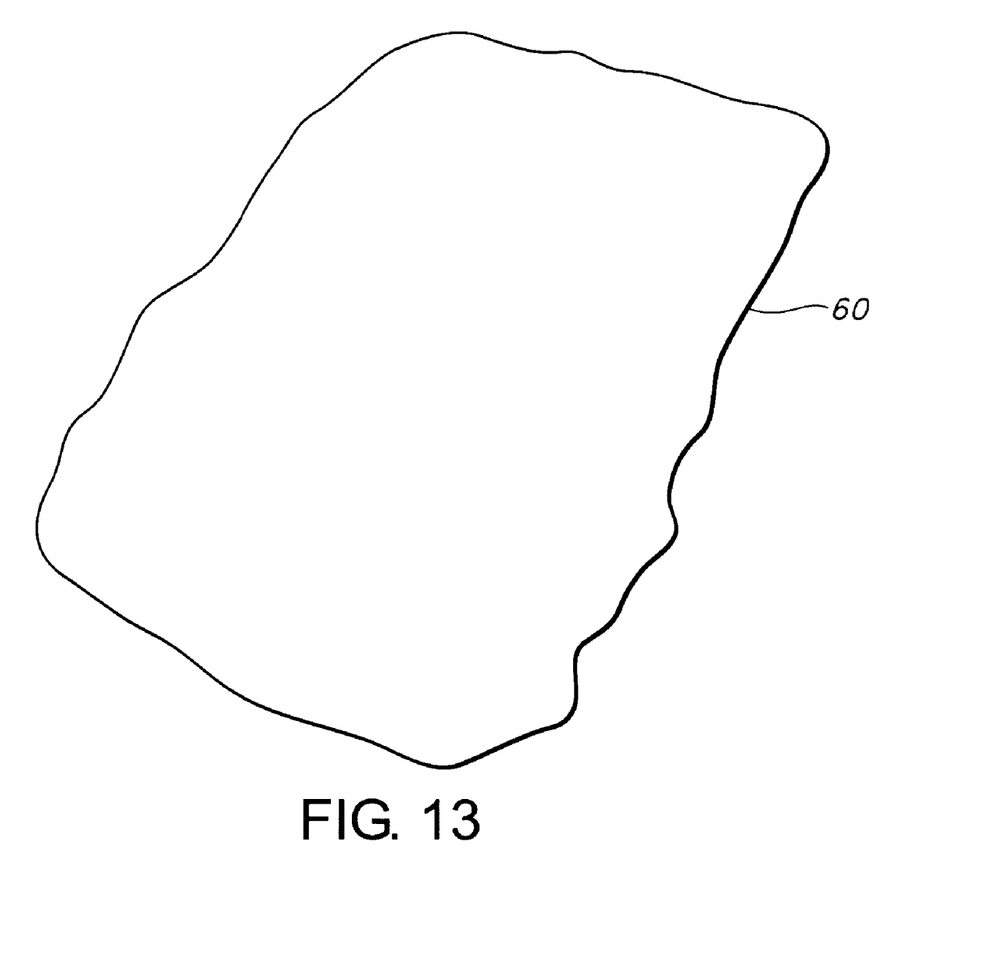
FIG. 13 is a perspective view of an ePTFE sheet structure of the present invention, the ePTFE sheet structure being made according to a method of the present invention.
Figure 14:
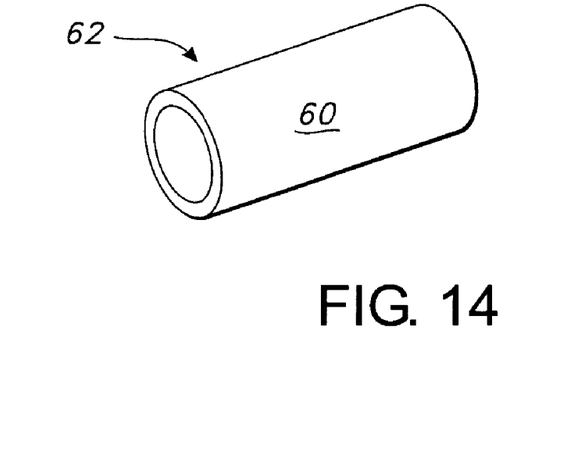
FIG. 14 is a perspective view of a vascular graft of the present invention, the vascular graft including an ePTFE tube structure formed from the sheet structure of FIG. 13.

The methods 10, 10a provide for the manufacture of an ePTFE sheet structure 60, as shown in FIG. 13. The sheet structure 60 is an integral, continuous structure as compared to the fabric material 55 which is formed by discrete filaments 52. The sheet structure 60 may be rolled and formed into a tube structure 62 in generally the same manner as described herein for the fabric material 55. The tube structure 62 may be used individually, or in combination with a stent 42 as a cover therefor, such as is shown in FIGS. 7 and 8. Alternatively, the tube structure 62 may be used as either of the tube structures 45, 47 shown in FIGS. 9 and 10. Alternatively, the sheet structure 60 may be shaped to have non-cylindrical contours, such as a planar or slightly curved, for use as an implant on the surface of or within the body of a patient.

The methods 10, 10a provide for the manufacture of vascular grafts which are suitable for use in devices for the treatment of abdominal and aortic aneurisms. Such devices may be referred to as "AAA devices". Vascular grafts made according to the methods 10, 10a are also suitable for use in medical procedures in which the grafts are installed through an opening in a patient's body which is substantial in size. Devices used in such procedures may be referred to as "open repair surgical products". Vascular grafts made according to the methods 10, 10a are also suitable for use in medical procedures in which the grafts are installed through a small opening such as may be made in minimally invasive surgery.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A method for making an ePTFE structure, said method comprising the steps of:

providing an unexpanded PTFE extrudate which is un-sintered;

initially expanding the un-sintered extrudate to produce an ePTFE structure having an initial node and fibril microstructure therein;

heating the ePTFE structure to raise the temperature thereof for a time period of sufficient duration such that at least a portion of the ePTFE structure is partially sintered, said heating step providing for the ePTFE structure to retain at least a portion of the initial expansion, said heating step further providing for limiting the temperature and time duration such that the portion of the ePTFE structure in which at least a portion of the initial expansion is retained is not fully sintered;

subsequently expanding the partially sintered ePTFE structure to produce a subsequent node and fibril microstructure therein; and heating the partially sintered ePTFE structure to raise the temperature thereof for a time period of sufficient duration to fully sinter the subsequently expanded ePTFE structure to completely lock the subsequent node and fibril micro-structure therein.

2. A method according to claim 1, wherein the unexpanded PTFE extrudate is defined by an unexpanded PTFE green tube extrudate, said providing step comprising the step of providing the unexpanded PTFE green tube extrudate, said initially expanding step producing an ePTFE tube structure from the unexpanded PTFE green tube extrudate.

3. A method according to claim 2, wherein said heating of the ePTFE tube structure comprises the step of raising the temperature thereof to between approximately 600 degrees F. and approximately 700 degrees F., said raising step being for a time duration of between approximately 1 minute and approximately 1 hour.

4. A method according to claim 2, wherein said initially expanding step increases the length of the PTFE green tube extrudate from between approximately 200% and approximately 6,000%.

5. A method according to claim 1 wherein said subsequent expanding step comprises the step of transversely expanding the partially sintered ePTFE structure.

6. A method according to claim 5, wherein the PTFE extrudate is defined by a PTFE green tube extrudate,
said providing step comprising the step of providing the PTFE green tube extrudate,
said initially expanding step being defined by the step of longitudinally expanding the PTFE green tube extrudate to produce an ePTFE tube structure,
said transversely expanding step being defined by the step of radially expanding the partially sintered ePTFE tube structure.

7. A method according to claim 6, wherein said radially expanding step increases the radial dimension of the partially sintered ePTFE tube structure from between approximately 10% and approximately 600%.

8. A method according to claim 1, wherein said heating of the ePTFE structure results in a semi-locked micro-structure thereof.

9. A method according to claim 2, and further comprising the step of initially heating the un-sintered PTFE green tube extrudate to a temperature of approximately 500 degrees F., said initially heating step being before said initially expanding step.

10. A method according to claim 2, and further comprising the step of assembling the ePTFE structure to a tube structure formed of a textile material, said assembling step being after said heating step, the ePTFE structure being in coaxial relation with the tube structure formed of the textile material.

11. A method for making an ePTFE structure, said method comprising the steps of:
providing an unexpanded PTFE extrudate which is un-sintered;
transversely expanding the un-sintered extrudate to produce an un-sintered ePTFE structure;
heating the ePTFE structure to raise the temperature thereof for a time period of sufficient duration such that at least a portion of the ePTFE structure is partially sintered, said heating step providing for the ePTFE structure to retain at least a portion of the transverse expansion, said heating step further providing for limiting the temperature and time duration such that the portion of the ePTFE structure in which at least a portion of the transverse expansion is retained is not fully sintered;
longitudinally expanding the un-sintered ePTFE structure to produce a node and fibril micro-structure therein; and
heating the partially sintered ePTFE structure to raise the temperature thereof for a time period of sufficient duration to fully sinter the longitudinally expanded ePTFE structure to completely lock the node and fibril micro-structure therein.

12. A method according to claim 11, wherein the PTFE extrudate is defined by a PTFE green tube extrudate,
said transversely expanding step being defined by the step of radially expanding the PTFE green tube extrudate to form an ePTFE tube structures,
said longitudinally expanding step being defined by the step of longitudinally expanding the ePTFE tube structure.

13. A method of forming a PTFE structure having a controlled crystalline polymer micro-structure, said method comprising the steps of:
providing a PTFE extrudate which is un-sintered;
initially expanding the un-sintered extrudate to produce an ePTFE structure;
heating at least a portion of the ePTFE structure for a time and at a temperature sufficient to partially sinter but insufficient to fully sinter the ePTFE structure;
permitting the ePTFE structure to cool and assume a micro-structure which is partially crystalline and which correlates to the conditions of partial sintering;
subsequently expanding the partially sintered ePTFE structure to produce a node and fibril micro-structure therein; and
heating the partially sintered ePTFE structure to raise the temperature thereof for a time period of sufficient duration to fully sinter the subsequently expanded ePTFE structure to completely lock the node and fibril micro-structure therein.

14. A method according to claim 13, and further comprising the step of determining the crystalline content of the micro-structure by DSC and comparing the determined crystalline content to the DSC for a fully crystallized micro-structure of the PTFE of the PTFE extrudate.

* * * * *